United States Patent [19]

Little et al.

[11] Patent Number: 5,391,759

[45] Date of Patent: Feb. 21, 1995

[54] PREPARATION OF 5-ACYLAMINO-1,2,4-TRIAZOLE-3-SULFONAMIDES

[75] Inventors: Jack C. Little, Lafayette; Mark J. Costales, Concord, both of Calif.; Ravi B. Shankar; R. Garth Pews, both of Midland, Mich.; Kidisti G. Mariam, Pittsburg; Susan D. Thompson, San Leandro, both of Calif.

[73] Assignee: DowElanco, Indianapolis, Ind.

[21] Appl. No.: 287,255

[22] Filed: Dec. 19, 1988

[51] Int. Cl.$^6$ .................................. C07D 249/02
[52] U.S. Cl. .................................. 548/263.8
[58] Field of Search ................. 548/263, 263.8

[56] References Cited

U.S. PATENT DOCUMENTS

| 2,554,816 | 5/1951 | Roblin | 544/263 |
| 2,744,907 | 5/1956 | Young | 544/263 |
| 4,038,387 | 7/1977 | Doyle, Jr. et al. | 544/263 |
| 4,148,626 | 4/1979 | Brooks et al. | 544/263 |
| 4,226,873 | 10/1980 | Kirkpatrick et al. | 544/263 |
| 4,278,793 | 7/1981 | Durckheimer | 544/263 |
| 4,734,123 | 3/1988 | Monte | 544/263 |
| 4,755,212 | 7/1988 | Kleschick et al. | 544/263 |

FOREIGN PATENT DOCUMENTS

| 244097A2 | 11/1987 | European Pat. Off. |  |
| 268951 | 6/1988 | European Pat. Off. |  |
| 3640155 | 5/1988 | Germany | 544/263 |

OTHER PUBLICATIONS

March, Advanced Organic Chemistry, pp. 445, 1087.
Avetisyan, Arm. Khm Zh. 34 781 (1981).
Abdel-Fattah, Egypt J. Chem. 27, 321 (1985) Abstract Only.
E. Grigat et al., Ger. Offen. 1,956,508, published May 19, 1971. (Chem. Abs).
R. O. Roblin, Jr. and J. W. Clapp, *J. Am Chem. Soc.*, 72, 4890-4892 (1950).
R. G. Shepark, *J. Organic Chem.*, 12, 275-283 (1947).
P. C. Guha and D. R. Mehta, *J. Indian Inst. Sci.*, 21A, 41-56 (1938).

*Primary Examiner*—Robert Gerstl
*Attorney, Agent, or Firm*—D. Wendell Osborne

[57] ABSTRACT

5-Acylamino-1,2,4-triazole-3-sulfonamides, which are useful intermediates for the preparation of 1,2,4-triazolo[1,5-a]pyrimidine-2-sulfonamide herbicides are prepared from 5-amino-3-mercapto-1,2,4-triazole by sequential acylation to 5-acylamino-3-mercapto-1,2,4-triazoles, chlorination to 5-acylamino-3-chlorosulfonyl-1,2,4-triazoles, and condensation with substituted anilines to 5-acylamino-1,2,4-triazole-3-sulfonamides. 5-Acylamino-3-chlorosulfonyl-1,2,4-triazole compounds are key intermediates in the process.

9 Claims, No Drawings

PREPARATION OF 5-ACYLAMINO-1,2,4-TRIAZOLE-3-SULFONAMIDES

BACKGROUND OF THE INVENTION

The present invention relates to a process for the preparation of 5-acylamino-1,2,4-triazole-3-sulfonamides utilizing 5-amino-3-mercapto-1,2,4-triazole, 5-acylamino-3-mercapto-1,2,4-triazoles, and/or 5-acylamino-3-chlorosulfonyl-1,2,4-triazoles as starting materials or intermediates.

Many 5-acylamino-1,2,4-triazole-3-sulfonamides, their preparation, and their value as intermediates in the manufacture of 1,2,4-triazolo[1,5-a]pyrimidine-2-sulfonamide herbicides have been described in U.S. Pat. Nos. 4,734,123 and 4,75 5,212. The only process disclosed for preparing these intermediates, however, involves the degradation of 1,2,4-triazolo[1,5-a]pyrimidine-2-sulfonamide compounds by oxidation and hydrolysis. This process is very expensive because it involves the preparation and degradation of one 1,2,4-triazolo[1,5-a]pyrimidine-2-sulfonamide compound in order to obtain another 1,2,4-triazolo[1,5-a]pyrimidine-2-sulfonamide compound.

The discovery of more direct, lower cost methods for the preparation of intermediates useful in the manufacture of 1,2,4-triazolo[1,5-a]pyrimidine-2-sulfonamide herbicides would be of great interest.

SUMMARY OF THE INVENTION

It has now been found that the readily available 5-amino-3-mercapto-1,2,4-triazole can be converted to 5-acylamino-1,2,4-triazole-3-sulfonamides, which are valuable intermediates for 1,2,4-triazolo-[1,5-a]pyrimidine-2-sulfonamide herbicides, by sequential acylation to obtain a 5-acylamino derivative, chlorination to obtain a 5-acylamino-3-chlorosulfonyl derivative, and condensation with substituted anilines to obtain a 5-acylamino-1,2,4-triazole-3-sulfonamide. The individual steps in the process can be practiced independently.

In the condensation step of the process of the present invention, a 5-acylamino-1,2,4-triazole-3-sulfonamide of Formula I

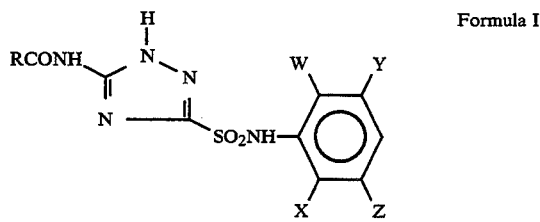

Formula I wherein
R represents H, $R^1$ or phenyl optionally containing up to 3 compatible substituents selected from F, Cl, Br, $CH_3$, and $CF_3$;
W represents F, Cl, Br, I, $R^1$, $SR^1$, $SOR^1$, $SO_2R^1$, $CO_2R^2$, CN, or $NO_2$;
X represents H, F, Cl, Br, I, $R^1$, $CH_2OR^1$, $OR^1$, $CO_2R^2$, $NO_2$, or a phenyl, phenoxy or 2-pyridinyloxy group each optionally containing up to 3 compatible substituents selected from F, Cl, Br, $CH_3$, and $CF_3$;
Y represents H, F, Cl, Br, I, $R^1$, or $CO_2R^2$;
Z represents H, F, Cl, Br, I, or $R^1$;
$R^1$ represents $C_1$-$C_4$ alkyl optionally containing one or more chloro or fluoro substituents; and
$R^2$ represents H, $C_1$-$C_4$ alkyl, $C_3$-$C_4$ alkenyl, or $C_3$-$C_4$ alkynyl, each optionally containing up to four compatible substituents selected from chloro, fluoro, $OR^1$, and phenyl is prepared by contacting a 5-acylamino-3-chlorosulfonyl-1,2,4-triazole of Formula II

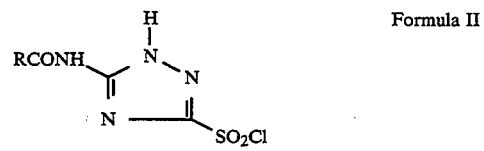

Formula II wherein R is as defined hereinabove with a substituted aniline of Formula III

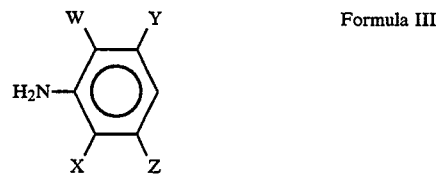

Formula III wherein W, X, Y, and Z are as defined hereinabove under conditions conducive to the formation of a compound of Formula I.

The compounds of Formula I can be further hydrolyzed to 5-amino-1,2,4-triazole-3-sulfonamide compounds of Formula IV,

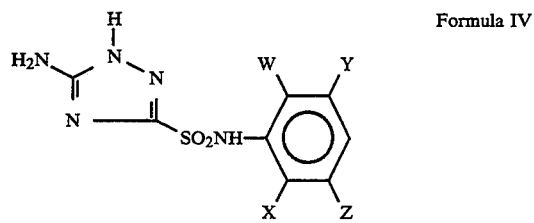

Formula IV wherein W, X, Y, and Z are as defined hereinabove, which, in turn, can be converted to substituted 1,2,4-triazolo[1,5-a]pyrimidine-2-sulfonamide herbicides by cyclization with 1,3-dicarbonyl compounds, in both cases using procedures known in the art.

The chlorination step of the process is carried out by contacting a 5-acylamino-3-mercapto-1,2,4-triazole compound of Formula V

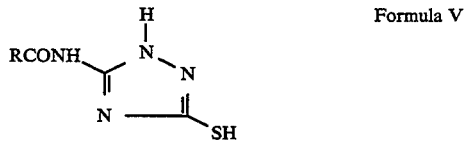

Formula V wherein R is as defined hereinbefore with chlorine in a medium containing an aqueous acid under conditions conducive to the formation of a 5-acylamino-3-chlorosulfonyl-1,2,4-triazole of Formula II.

The compounds of Formula V can be obtained by acylation of 5-amino-3-mercapto-1,2,4-triazole with a suitable acylating agent such as a carboxylic acid chloride (RCOCl), a carboxylic acid anhydride ((RCO)$_2$O), a carboxylic acid (RCO$_2$H), a carboxylate ester (RCO$_2$R), or a carboxamide (RCONH$_2$), wherein R is as defined hereinabove, under conditions conducive to the formation of the mono-acylated product of Formula V.

Any two or all of the process steps of acylation of 5-amino-3-mercapto-1,2,4-triazole to obtain a compound of Formula V, chlorination of a compound of Formula V to obtain a compound of Formula II, and condensation of a compound of Formula II with a compound of Formula III to obtain a compound of Formula I can be conducted consecutively without separation and recovery of the intermediate compounds of Formulas V and III when the reactants and reaction media are selected to be compatible.

The 5-acylamino-3-chlorosulfonyl-1,2,4-triazole compounds of Formula II are intermediates which are important to the overall invention.

DETAILED DESCRIPTION OF THE INVENTION

The overall process of the present invention takes advantage of the availability and low cost of 5-amino-3-mercapto-1,2,4-triazole (a compound that possesses several possible tautomeric forms and is alternately named 5-amino-2,4-dihydro-3H-1,2,4-triazole-3-thione), which is well known in the art, as a starting material for the preparation of substituted 1,2,4-triazolo[1,5-a]pyrimidine-2-sulfonamide herbicides. The process of the invention involves several chemical reaction steps. These reaction steps can be carried out in sequence to obtain the desired herbicidal products. Alternately, the separate steps can be carried out individually, and independently, for example, to prepare any of the compounds of Formula I, II, IV, or V or to prepare a substituted 1,2,4-triazolo[1,5-a]pyrimidine-2-sulfonamide herbicide from any one of the indicated intermediates as a starting material.

The acylated derivatives of Formula V wherein R represents H, $C_1$-$C_4$ alkyl optionally containing one or more chloro or fluoro substituents, or phenyl optionally containing up to 3 compatible substituents selected from F, Cl, Br, $CH_3$, and $CF_3$ can be obtained from 5-amino-3-mercapto-1,2,4-triazole by acylation with an acyl halide (RCOCl), a carboxylic acid anhydride ($(RCO)_2O$), or a carboxylic acid ($RCO_2H$), a carboxylate ester ($RCO_2R$), or a carboxamide ($RCONH_2$) wherein R, in each instance, is as hereinbefore defined. A suitable acylating agent is employed based on availability, reactivity and other usual considerations. The reaction is carried out in an essentially non-aqueous medium under conditions conducive to the formation of the a compound of Formula V, which is the thermodynamically most stable mono-acylated product. In one preferred procedure, a mixture of 5-amino-3-mercapto-1,2,4-triazole and an appropriate carboxylic acid anhydride in an excess of the carboxylic acid from which the anhydride is derived is heated to effect the desired acylation. The reaction can be depicted as follows:

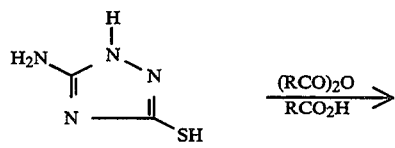

5-amino-3-mercapto-1,2,4-triazole

-continued

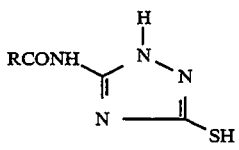

Formula V

The product of Formula V can be recovered by cooling and filtering or by other conventional means. The carboxylic acid anhydride is generally used in at least equimolar quantities and more often is used in an excess of about 5 to about 80 percent. The reaction is generally conducted at a temperature of about 50° C. to about 180° C., usually at about 80° C. to about 150° C. and it is generally complete in about 1 to about 24 hours, usually about 2 to about 8 hours. A catalyst, such as pyridine, can sometimes be advantageously employed. Acetic anhydride is a preferred acylating agent using this procedure.

With some less reactive acyl groups, such as benzoyl, it is often preferred to use the appropriate acyl chloride rather than the dicarboxylic anhydride. In this procedure 5-amino-3-mercapto-1,2,4-triazole is combined with the acyl chloride in essentially waterfree excess pyridine or methylated pyridine and the mixture heated to effect acylation to a compound of Formula V. The product can be recovered by conventional means, such as filtration. The acyl chloride is generally employed in excess, usually in about 3 to about 50 percent excess. The reagents are typically combined at ambient temperature or below and subsequently heated in the range of about 80° C. to about 150° C. or the reflux temperature of the mixture. The reaction is typically complete in about 1 to about 24 hours. Benzoyl chloride is a preferred acylating agent in this procedure.

In the case of formylation and acylation with other highly reactive acyl groups, the conversion of 5-amino-3-mercapto-1,2,4-triazole to the compound of Formula V (R=H) is often best carried out by heating 5-amino-3-mercapto-1,2,4-triazole with excess formic acid or other highly reactive carboxylic acid. The product can be recovered by conventional means, such as by cooling and filtering. The reaction takes place at about 50° C. to about 120° C. and is preferably carried out at the reflux temperature of the medium under atmospheric pressure. Sufficient carboxylic acid, such as formic acid, is generally employed to permit good mixing. The formyl compound of Formula V is of special interest because of its ease of preparation and the ease of removal of the formyl group from the compounds of Formula I derived from it.

The 3-chlorosulfonyl compounds of Formula IV wherein R represents H, $C_1$-$C_4$ alkyl optionally containing one or more chloro or fluoro substituents, or phenyl optionally containing up to 3 compatible substituents selected from F, Cl, Br, $CH_3$, and $CF_3$ can be obtained by chlorination of an appropriate compound of Formula V under conditions conducive to the reaction. The reaction can be depicted as follows:

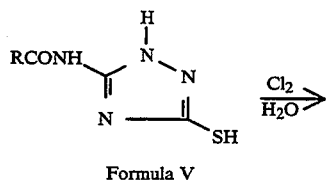

Formula V

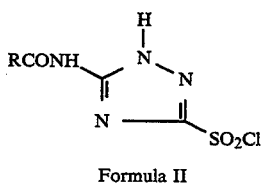

Formula II

The conversion is generally effected by treating a compound of Formula V with chlorine in an aqueous acid medium until the reaction is substantially complete. Agitation is generally employed to promote contact of the reagents. The temperature is generally maintained in the range of about the freezing point of the mixture to about 50° C. It is preferably maintained at about −15° C. to about 30° C. and more preferably at about −5° C. to about 25° C. External cooling is generally employed as the reaction is exothermic.

The reaction theoretically requires three moles of chlorine per mole of the compound of Formula V. Chlorine amounts of from about 2.8 to about 3.6 moles per mole of compound of Formula V are typically employed and amounts of about 2.9 to about 3.3 are preferred. The reaction generally takes place about as fast as the chlorine can be added and chlorine is usually added until uptake virtually ceases, which occurs at about 3 moles.

The reaction generates hydrochloric acid as a by-product and hydrochloric acid is, therefore, always present during the process. Acids are also generally employed in the initial reaction medium. Suitable acids that can be employed include strong mineral acids, such as hydrochloric, sulfuric, and phosphoric acids, and organic acids, such as formic, acetic, propionic, trifluoroacetic, and methanesulfonic acids. The acids can be employed in combination. Suitable acids are those that facilitate the conversion of a 3-mercapto group to a 3-chlorosulfonyl group but do not unduly catalyze hydrolysis or extrusion of sulfur dioxide or other reactions of the product of Formula II and whose aqueous mixtures are liquid solutions. It is generally preferred to employ aqueous hydrochloric acid.

About 1 to about 37 percent hydrochloric acid is typically employed as the chlorination medium. Initial concentrations of about 2 to about 30 percent hydrochloric acid are preferred and those of about 10 to about 20 percent are especially preferred. The medium increases in acid concentration during the reaction due to production of hydrochloric acid as a by-product.

When the chlorination step is carried out in a medium containing an aqueous carboxylic acid, such as formic or acetic acid, the medium can be varied between acid containing about 1.5 moles of water per mole of 5-amino-3-mercapto-1,2,4-triazole to be chlorinated and mixtures of water and formic or acetic acid containing about 95 percent water. It is often preferred to employ formic acid or acetic acid containing about 2 (the theoretical amount) to about 10 moles of water per mole of 5-acylamino-3-mercapto-1,2,4-triazole or to employ mixtures of water and formic or acetic acid containing about 10 to about 50 percent of the acid. Hydrochloric acid is often advantageously employed in conjunction with aqueous formic or acetic acid. In one procedure about one mole of hydrochloric acid is employed per mole of 5-acylamino-3-mercapto-1,2,4-triazole.

About a liter of aqueous acid containing medium is generally employed for each 30 g to 250 g of compound of Formula V chlorinated. Inert, immiscible organic solvents can be employed in combination with the aqueous acid.

The product compounds of Formula II can be recovered by conventional means, such as by filtration or centrifugation. They are best used or recovered and dried quickly after the chlorine addition is complete in order to avoid yield losses due to hydrolysis or sulfur dioxide evolution.

The condensation of compounds of Formula II with substituted anilines of Formula III to obtain compounds of Formula I wherein R represents H, $C_1$-$C_4$ alkyl optionally containing one or more chloro or fluoro substituents, or phenyl optionally containing up to 3 compatible substituents selected from F, Cl, Br, $CH_3$, and $CF_3$; W represents F, Cl, Br, I, $R^1$, $SR^1$, $SOR^1$, $SO_2R^1$, $CO_2R^2$, CN or $NO_2$; X represents H, F, Cl, Br, I, $R^1$, $CH_2OR^1$, $OR^1$, $CO_5R^2$, $NO_2$, or a phenyl, phenoxy, or 2-pyridinyloxy group each optionally containing up to 3 compatible substituents selected from F, Cl, Br, $CH_3$, and $CF_3$; Y represents H, F, Cl, Br, I, $R^1$, or $CO_2R^2$; Z represents H, F, Cl, Br, I, or $R^1$; $R^1$ represents $C_1$-$C_4$ alkyl optionally containing one or more chloro or fluoro substituents; and $R^2$ represents H, $C_1$-$C_4$ alkyl, $C_3$-$C_4$ alkenyl, or $C_3$-$C_4$ alkynyl, each optionally containing up to four compatible substituents selected from chloro, fluoro, $OR^1$, and phenyl is effected by allowing the two reactants to react under conditions conducive to the formation of the compound of Formula I. The reaction can be depicted as follows:

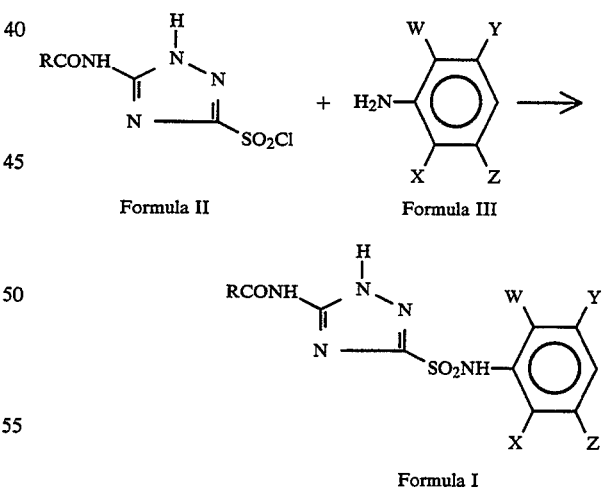

The process is sometimes conducted by combining appropriate compounds of Formulas II and III in the presence of an organic solvent and an acid scavenging, but otherwise unreactive base or excess substituted aniline of Formula III and heating with agitation until a recoverable amount of the compound of Formula I is obtained. Approximately equimolar quantities of the two reactants or up to about a 100 percent excess of the substituted aniline are generally employed. Tertiary amine bases, including pyridine type bases, such as pyridine, gamma-picoline and other methylated pyridines, trialkylamines, such as triethylamine and N-methylmorpholine, and dialkylarylamines, such as N,N-dimethylaniline, can be employed as the acid scavenging base. Certain inorganic bases, including alkali metal salts of carboxylic acids, such as sodium acetate, and alkali metal carbonates, such as potassium carbonate are also sometimes employed. Pyridine can be used as both base and solvent and is often preferred. Other tertiary amine bases are typically used in approximately equimolar amounts to the compound of Formula II.

Organic solvents that at least slightly dissolve the reactants and which are substantially inert to the reactants and products, such as acetic acid, formic acid, and acetonitrile, are generally employed. The process is usually conducted in a substantially dry atmosphere with agitation.

Temperatures of about 40° C. to about 130° C. are generally employed and temperatures of about 60° C. to about 100° C. are preferred. The reaction is typically complete in about 1 to about 48 hours and more often in about 2 to about 8 hours.

The product of Formula I can be recovered by conventional means, such as by extracting the product into an aqueous alkaline medium and then reprecipitating it from that medium with acid and recovering the solid that forms by filtration or centrifugation.

It is possible to conduct several steps of the overall process consecutively without recovering intermediates prepared in each step from the mixture obtained. This is an advantageous aspect, of the invention because it reduces the number of operations, the recycle of solvents, and the amount of waste produced. Thus, any or all of the contiguous steps of acylation of 5-amino-3-mercapto-1,2,4-triazole to a 5-acylamino-3-mercapto-1,2,4-triazole of Formula V, chlorination to a 5-acylamino-3-chlorosulfonyl-1,2,4-triazole of Formula II, condensation with a substituted aniline to a 5-acylamino-1,2,4-triazole-3-sulfonamide of Formula I, and hydrolysis to a 5-amino-1,2,4-triazole-3-sulfonamide of Formula IV can be carried out consecutively without recovery of intermediates when appropriate reaction media for each are selected to be compatible. A preferred form of this embodiment involves the selection of formic acid or acetic acid containing about 2 to about 10 moles of water per mole of 5-acylamino-3-mercapto-1,2,4-triazole (compound of Formula V) to be chlorinated to be the aqueous acid present in the chlorination step of the overall process (preparation of a compound of Formula II). In this preferred form, R usually represents hydrogen or methyl in Formulas I, II, and V. It is, as is pointed out hereinabove, possible to prepare 5-acylamino-3-mercapto-1,2,4-triazole compounds of Formula V by acetylation of 5-amino-3-mercapto-1,2,4-triazole with acetic anhydride in a medium containing acetic acid or by formylation with excess formic acid. It is also possible to condense compounds of Formula II with a substituted aniline of Formula III to obtain a compound of Formula I using formic acid or acetic acid as a solvent. The condensation is typically carried out using excess substituted aniline or an alkali metal formate or acetate as the acid scavenging base. It is further possible to hydrolyze a compound of Formula I to a compound of Formula IV in a formic acid or acetic acid based medium after the addition of aqueous mineral acid.

Alternately, compounds of Formula I can be obtained from the chlorosulfonyl compounds of Formula II by condensation of compounds of Formula II with N-trialkylsilylanilines derived from the substituted anilines of Formula III, using conditions similar to those described in the art for other heterocyclic sulfonyl chlorides.

The compounds of Formula I can be hydrolyzed to obtain compounds of Formula IV using the procedures disclosed in U.S. Pat. No. 4,734,123, the appropriate descriptions of which are hereby incorporated by reference. The reaction removes the RCO moiety of the compound of Formula I and replaces it with a proton.

The compounds of Formula IV can be cyclo-condensed with 1,3-dicarbonyl compounds to obtain herbicidal substituted 1,2,4-triazolo[1,5-a]pyrimidine-2-sulfonamide herbicides of Formula VI, which are disclosed in U.S. Pat. No. 4,755,212.

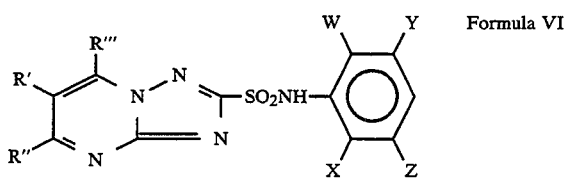

Formula VI

The condensation can be carried out as described in U.S. Pat. Nos. 4,734,123 and 4,755,212, the appropriate portions of which are hereby incorporated by reference.

The following examples are presented to illustrate the invention and should not be construed as limiting the scope of the invention. All melting points are uncorrected.

EXAMPLE 1

Preparation of 5-Benzoylamino-3-mercapto-1,2,4,-triazole (Formula V, R=phenyl)

To a suitably equipped reaction vessel was charged 116 g (1.0 mole) of 5-amino-3-mercapto-1,2,4-triazole and 500 ml of pyridine. A total of 147.5 g (1.05 mole) of benzoyl chloride was added with vigorous stirring over 25 minutes, during which time the temperature rose from 24° to 59° C. The mobile, pale yellow slurry obtained was heated at reflux with stirring. The solid material dissolved and then, after about 40 additional minutes, a white solid began separating. An additional 200 ml of pyridine was added to aid mixing and the reaction was continued at 117°–122° for a total of 7 hours. The thick, white slurry obtained was filtered, washed with water and with methylene chloride, and dried to obtain 186 g (84 percent of theory) of the title compound, m.p. 311°–312° (dec.).

Elemental analysis (typical sample): Calc. for $C_9H_8N_4OS$ %C, 47.4; %H, 3.92; %N, 24.6 Found %C, 47.5; %H, 3.61; %N, 24.4 $^{13}C$ NMR: $\delta = 165.90, 165.40, 145.00, 132.68, 131.98, 128.56,$ and $127.96$ $^1H$ NMR: $\delta = 8.50 - 7.90$ (m, 2H) and $7.72 - 7.61$ (m, 3H)

EXAMPLE 2

Preparation of 5-Benzoylamino-3-chlorosulfonyl-1,2,4-triazole (Formula II, R=phenyl)

A reactor was charged with 61 g (0.28 mole) of 5-benzoylamino-3-mercapto-1,2,4-triazole and 1 l of 1N hydrochloric acid. The resultant slurry was chilled to −5° C., and a total of 83 g (0.8 mole) of chlorine gas was added through a fritted glass sparger over 40 minutes while maintaining the temperature at −6° to 4° C. by means of an ice/salt bath. The resulting solids were recovered by filtration, washed with cold water, and dried to obtain 64 g (80 percent of theory) of the title compound as a pale yellow solid, m.p. 203°–205° (dec.). A sample purified by recrystallization from acetonitrile was white needles melting at 209°–210° C. The carbon nmr spectrum was consistent with the assigned structure.

EXAMPLE 3

Preparation of 5-Benzoylamino-3-chlorosulfonyl-1,2,4-triazole (Formula II, R=phenyl)

In a manner similar to that described in Example 2, 66 g (0.3 mole) of 5-benzoylamino-3-mercapto-1,2,4-triazole in 1.5 l of 40 percent aqueous acetic acid was chlorinated over 30 minutes at $-2$ to $+1°$ C. with 64 g (0.9 mole) of gaseous chlorine to obtain a slurry, which after filtering, washing with water, and drying in a vacuum oven at 50°–55° for 24 hours produced a total of 74g (86 percent of theory) of the title compound melting at 200°–203° C. (dec.). Melting points as high as 205°–207° C. were determined on other samples.

Elemental analysis (typical sample): Calc. for $C_9H_7ClN_4O_3S$ %C, 38.0; %H, 2.46; %N, 19.5 Found %C, 38.3; %H, 2.57; %N, 19.6 $^{13}C$ NMR: $\delta = 165.47$, 159.81, 150.12, 132.46, 132.39, 128.52, and 127.94. $^1H$ NMR: $\delta = 8.05$–7.90 (d, 2H, J=10.1) and 7.85–7.62 (m, 3H).

EXAMPLE 4

Preparation of 5-Benzoylamino-N-(2,6-dichlorophenyl)-1,2,4-triazole-3-sulfonamide (Formula I, R=phenyl, W and X=Cl, and Y and Z=H)

A small flask equipped with a magnetic stirrer and protected from the atmosphere by a drying tube was charged with 8.1 g (0.05 mole) of 2,6-dichloroaniline, 20 ml of dry pyridine and then 14.4 g (0.05 mole) of dry 5-benzoylamino-3-chlorosulfonyl-1,2,4-triazole was added over about 1 minute with vigorous stirring. After the exotherm had subsided somewhat, the mixture was heated with an oil bath maintained at 100°–106° C. for 3 hours with stirring. The mixture was next concentrated under reduced pressure on a rotary evaporator to remove the bulk of the pyridine (80° C./1 mm) and then taken up in a mixture of 25 ml of concentrated aqueous ammonia, 125 ml of water and 100 ml of methylene chloride. After cooling and filtration to remove the insoluble material, the methylene chloride phase was removed and the pH of the aqueous phase was adjusted to 2.5 with hydrochloric acid. The precipitate that formed was collected by filtration, washed with watery and dried to obtain 10.2 g (50 percent of theory) of the title sulfonamide. A sample purified by recrystallization from acetonitrile melted at 321°–322° (dec.). The carbon nmr spectrum was consistent with the assigned structure, having absorptions at 159.2, 149.7, 165.6, 135.9, 130.8, 128.9, 130.0, 132.8, 128.6, 128.1, and 131.7 ppm.

EXAMPLE 5

Preparation of 5-Amino-N-(2,6-dichlorophenyl)-1,2,4-triazole-3-sulfonamide (Formula IV, W and X=Cl and Y and Z=H)

A mixture of 34.7 g (0.084 mole) of 3-benzoylamino-N-(2,6-dichlorophenyl)-1,2,4-triazole-5-sulfonamide and 200 ml of 10 percent sodium hydroxide was heated at reflux for 14 hours. It was then treated with decolorizing charcoal and acidified to pH 10 with hydrochloric acid to obtain a flocculent precipitate. This was removed by filtration and discarded. Upon further acidification to pH 6.0 an ivory solid formed which was recovered by filtration, washed with water, and dried to obtain 13.3 g (50 percent of theory) of the title compound as a white solid. A purified sample prepared by re-precipitation with hydrochloric acid from a solution in aqueous sodium hydroxide had a melting point of 268°–269° (dec.). The carbon nmr spectrum was consistent with the assigned structure and the melting point with that reported in the art.

EXAMPLE 6

Preparation of 5-Benzoylamino-N-(2,6-difluorophenyl)-1,2,4-triazole-3-sulfonamide (Formula I, R=phenyl, W and X=F, and Y and Z=H)

A small flask equipped with a magnetic stirrer and protected from the air by a drying tube was charged with 6.5 g (0.05 mole) of 2,6-difluoroaniline and 20 ml of dry pyridine. To this was then added, with stirring, 14.4 g (0.05 mole) of dry 3-benzoylamino-3-chlorosulfonyl-1,2,4-triazole over 3 minutes. After the mild exotherm had subsided, the mixture was heated to 75° C. for 21 hours. It was then cooled and dispersed between 120 ml of dilute aqueous ammonia and 100 ml of methylene chloride. The dark solvent layer was removed and discarded. A second extraction with methylene chloride gave a much lighter solvent layer, leaving a dark aqueous phase. The latter was acidified to pH 5.5 with hydrochloric acid to give 9.2 g (49 percent of theory) of the title compound as a white solid, m.p. 312°–315° C. (dec.). The carbon nmr spectrum was consistent with the assigned structure. A similarly prepared sample had consistent proton and carbon nmr spectra and C, H, and N analysis.

EXAMPLE 7

Preparation of 5-Amino-N-(2,6-difluorophenyl)-1,2,4-triazole-3-sulfonamide (Formula IV, W and X=F, Y and Z=H)

A mixture of 16.9 g (0.045 mole) of 5-benzoylamino-N-(2,6-difluorophenyl)-1,2,4-triazole-3-sulfonamide and 75 ml of 6N sodium hydroxide was heated to reflux for a total of 4 hours. The resulting solution was treated witch decolorizing carbon, filtered, and acidified with hydrochloric acid. The solids that formed were collected by filtration and dried to obtain a total of 14.8 g of crude product. This material was taken up dilute aqueous sodium hydroxide, treated again with decolorizing carbon, filtered and acidified to pH 5.0. The resulting slurry was chilled and the solids collected by filtration and dried to obtain 9.0 g of the title compound as a white solid, m.p. 255°–257° (dec.). The carbon nmr spectrum was consistent with the assigned structure and the melting point with that in the art.

EXAMPLE 8

Preparation of 5-Acetylamino-3-mercapto-1,2,4-triazole (Formula V, R=CH₃)

To a 2 l, 3-necked flask equipped with an efficient stirrer, reflux condenser, and thermometer was added 116 g (1.0 mole) of 5-amino-3-mercapto-1,2,4-triazole, 1 l of glacial acetic acid and 153 g (1.5 moles) of acetic anhydride. The mixture was heated to reflux (118°–120°) with stirring for 2 hours and then cooled to about 10° C. Recovery of the solids present by filtration and drying resulted in about 102 g (65 percent of theory) of the title compound, m.p. 326°–328° (dec.), a white, crystalline solid. A sample purified by washing with 2-propanol and drying melted at 336° C. (dec.). The carbon nmr spectrum of this compound was consistent with the assigned structure, having absorptions at 169.29, 164.99, 144.77, and 22.73 ppm as were the proton nmr spectrum, having an absorption at −2.00 ppm, and the elemental (C, H, and N) analysis.

EXAMPLE 9

Preparation of 5-Acetylamino-3-chlorosulfonyl-1,2,4-triazole (Formula II, R=CH$_3$)

A 3 l, 3-necked flask equipped with an efficient stirrer, thermometer, cooling bath, fritted glass gas inlet tube, and aqueous sodium hydroxide scrubber was charged with 79 g (0.5 mole) of 5-acetylamino-3-mercapto-1,2,4-triazole and 250 ml of 10 percent aqueous hydrochloric acid. The mixture was chilled to −5° C. and chlorine gas addition was initiated with good stirring. A total of 114 g (1.6 mole) of chlorine was added over 1.7 hours with the temperature being maintained at −3° to −10° C. The mixture was allowed to stir briefly while warming to 15° C. and was then filtered. The solids obtained were washed with cold water and dried to obtain the title compound as a white solid melting at 184°–184.5° C. The yield was 90.4 g (81 percent of theory). The carbon nmr spectrum was consistent with the assigned structure, having absorptions at 161.0, 151.3, 170.8, and 22.9 ppm.

A sample of this compound was purified by dissolving it in acetone, filtering to remove solids, and removing the acetone by evaporation. It melted at 177° C. with decomposition.

Calc. for C$_4$H$_4$ClN$_4$O$_3$S %C, 21.5; %H, 1.80; %N, 25.1 Found %C, 21.3; %H, 2.20; %N, 25.1

EXAMPLE 10

Preparation of N-(2,6-dichloro-3-methylphenyl)-5-acetylamino-1,2,4-triazole-3-sulfonamide (Formula I, R=CH$_3$, W and X=Cl, Y=CH$_3$, and Z=H)

A 250 ml, 1-necked flask equipped with a magnetic stirrer and filled with nitrogen gas was charged with 15 ml of dry pyridine and 8.8 g (0.05 mole) of 2,6-dichloro-3-methylaniline. To the stirred solution was added 11.3 g (0.05 mole) of crude 5-acetylamino-3-chlorosulfonyl-1,2,4-triazole over 10–30 minutes. The resulting dark green mixture, which had a mild exotherm during the addition, was heated to 100°–105° C. with stirring for 3–4 hours. It was then dispersed between a mixture of methylene chloride and dilute aqueous sodium hydroxide and the organic layer was removed. Acidification of the aqueous phase and filtraton and drying of the precipitate that formed gave the title sulfonamide as a tan solid melting at 284° (dec.). The yield was 60 percent of theory. A sample of this compound which was recrystallized from a mixture of methanol and water was a pale ivory powder melting at 285°–285.5° C. (dec.) and had the following elemental analysis: Calc. for C$_{11}$H$_{11}$Cl$_2$N$_5$O$_3$S %C, 36.3; %H, 3.04; %N, 19.23 Found 36.3; %H, 3.08; %N, 19.65

The carbon nmr spectrum was consistent with the assigned structure, having absorptions at 159.4, 157.5, 136.0, 132.9, 135.9, 130.7, 131.0, 127.6, and 20.1 ppm.

EXAMPLE 11

Preparation of 5-Formylamino-3-mercapto-1,2,4-triazole (Formula V, R=H)

A 500 ml, 3-necked flask equipped with a mechanical stirrer, a reflux condenser with nitrogen outlet and a thermometer was charged with 24.4 g (0.2 mole of 95 percent) of 5-amino-3-mercapto-1,2,4-triazole and 140 ml of formic acid. The mixture was heated to reflux with stirring for 4 hours and allowed to cool to room temperature. The solids present were collected by filtration, washed with water, and dried to obtain 28.2 g (98 percent of theory) of the title compound as a white solid, m.p. 260°–262° C. The infrared spectrum was consistent with the assigned structure, having a carbonyl stretch at 1700 cm−1, as was the mass spectrum, having a parent peak at 144 (M+).

EXAMPLE 12

Preparation of 5-Formylamino-3-chlorosulfonyl-1,2,4-triazole (Formula II, R=H)

A 500 ml, 4-necked flask equipped with a mechanical stirrer, a sparge tube to introduce chlorine, a low temperature thermometer and a nitrogen outlet was charged with 7 g (48.6 mmol) of 5-formylamino-3-mercapto-1,2,4-triazole and 150 ml of 0.5M aqueous hydrochloric acid. The mixture was cooled to 0° C. with stirring and chlorine gas (160 mmol) was bubbled through while maintaining the temperature below 5° C. The mixture was diluted with water (20 ml), filtered, and the solids obtained dried to obtain 8.8 g (86 percent of theory) of the title compound as a white solid, m.p. 194°–196° C. The infrared spectrum was consistent with the assigned structure, having chlorosulfonyl associated absorptions at 1400 and 1175 cm−1, as was the mass spectrum, having a parent peak at 212 (M+).

EXAMPLE 13

Preparation of N-(2,6-Difluorophenyl)-5-formylamino-1,2,4-triazole-3-sulfonamide (Formula I, R=H, W and X=F, and Y and Z=H)

To a mixture of 1.3 g (10 mmol) of 2,6-difluoroaniline in 4 ml of pyridine was added 1.94 g (9.2 mmol) of 5-formylamino-3-chlorosulfonyl-1,2,4-triazole over a period of 5 minutes. The mixture was heated with stirring to 70° C. for 4 hours. It was then cooled and dispersed between 25 ml of 1N aqueous sodium hydroxide and 50 ml of chloroform. The aqueous layer was acidified with aqueous hydrochloric acid and filtered. The solids collected were dried to obtain 167 g (60 percent of theory) of the title compound, m.p. 258°–260° C. The infrared spectrum was consistent with the assigned structure.

EXAMPLE 14

Preparation of N-(2,6-Dichloro-3-methylphenyl)-5-formylamino-1,2,4-triazole-5-sulfonamide (Formula I, R=H, W and X=Cl, Y=CH$_3$, and Z=H)

To a mixture of 1 g (5.2 mmol) of 2,6-dichloro-3-methylaniline in 2 ml pyridine was added 1 g (4.7 mmol) of 5-formylamino-3-chlorosulfonyl-1,2,4-triazole over a period of 5 minutes. The mixture was heated with stirring to 70° C. for 4 hours. It was then cooled and dispersed between 25 ml of 1N aqueous sodium hydroxide and 50 ml of chloroform. The aqueous layer was recovered, extracted with more chloroform, and acidified with aqueous hydrochloric acid. The solids that formed were collected by filtration and dried to obtain 1.0 g (59 percent of theory) of the title compound, m.p. 275°–279° C. The infrared and carbon nmr spectra were consistent with the assigned structure.

EXAMPLE 15

Preparation of 5-Amino-N-(2,6-dichloro-3-methylphenyl)-1,2,4-triazole-3-sulfonamide (Formula IV, W and X=Cl, Y=CH₃, and Z=H)

A mixture of 3.5 g (10 mmol) of 5-formylamino-N-(2,6-dichloro-3-methylphenyl)-1,2,4-triazole-3-sulfonamide and 50 ml of 1 percent aqueous sodium hydroxide was heated to reflux for 4 hours and was then cooled and acidified with dilute aqueous hydrochloric acid. The solids that formed were collected by filtration and dried to obtain 2.77 g (86 percent of theory) of the title compound, m.p. 243°–44° C. The proton and carbon nmr spectra were consistent with the assigned structure.

EXAMPLE 16

Preparation of N-(2,6-dichloro-3-methylphenyl)-5-amino-1,2,4-triazole-3-sulfonamide (Formula IV, W and X=Cl, Y=CH₃, and Z=H)

A mixture of 11.6 g (0.10 mole) of 5-amino-3-mercapto-1,2,4-triazole, 12.75 g (0.0125 moles) of acetic anhydride and 100 ml of acetic acid was prepared and heated at reflux with stirring for 12 hours. Another 50 ml of acetic acid and 10 ml of water were then added and the mixture was cooled to 12° C. Chlorine (21 g, 0.3 mole) was then added to the mixture with stirring over a 15 min. period at 12°–20° C. A yellow solution was obtained. About 100 ml of volatiles were removed by distillation at 50° C. under reduced pressure. The resulting residue was combined with 2,6-dichloro-3-methylaniline (14.1 g, 0.080 mole) and the mixture heated at 115° C. for 4 hours with stirring. Concentrated aqueous hydrochloric acid (50 ml) was then added and the mixture was heated at reflux with stirring for another 5 hours. It was then allowed to cool to ambient temperature and the solids present were collected by filtration. The collected solids were placed in 200 ml of 10 percent aqueous sodium hydroxide. The insoluble material was removed by filtration and the pH of the filtrate was adjusted to 4.5 with hydrochloric acid to reprecipitate the title compound. The solids were recovered by filtration, washed with water, and dried under reduced pressure to obtain 10.1 g (28.9 percent of theory) of the title compound assaying 95 percent by high pressure liquid chromatography.

EXAMPLE 17

Preparation of N-(2,6-dichloro-3-methylphenyl)-5-amino-1,2,4-triazole-3-sulfonamide (Formula IV, W and X=Cl, Y=CH₃, and Z=H)

5-Acetylamino-3-mercapto-1,2,4-triazole (15.6 g, 0.10 mole) was added to 250 ml of acetic acid containing 3.6 g (0.20 mole) of water. The mixture was cooled to 15° C. with an external ice bath and 21 g (0.30 mole) of chlorine was added as a gas under the surface of the liquid with stirring over a 30 min. period. About 200 ml of volatiles were then removed from the mixture by evaporation under reduced pressure at up to 120° C. The residue was combined with 17.6 g (0.10 mole) of 2,6-dichloro-3-methylaniline and the mixture heated with stirring at 115° C. for 9 hours. A 100 ml portion of water and 25 ml of concentrated aqueous hydrochloric acid were added and the mixture heated at reflux for 12 hours. It was then allowed to cool and the solids present were collected by filtration. The solids were then placed in 200 ml of 10 percent aqueous sodium hydroxide and the insoluble fraction removed by filtration. The filtrate was acidfied with aqueous hydrochloric acid to pH 4.5 and the solids that formed were recovered by filtration and dried under reduced pressure to obtain 8.9 g (20 percent of theory) of the title compound assaying 80 percent purity by high pressure liquid chromatography.

What is claimed is:

1. A process for preparing a 5-acylamino-1,2,4-triazole-3-sulfonamide compound of the formula

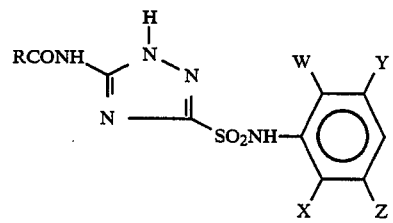

wherein

R represents H, $R^1$, or phenyl optionally containing up to 3 compatible substituents selected from F, Cl, Br, CH₃, and CF₃;

W represents F, Cl, Br, I, $R^1$, $SR^1$, $SOR^1$, $SO_2R^1$, $CO_2R^2$, CN, or $NO_2$;

X represents H, F, Cl, Br, I, $R^1$, $CH_2OR^1$, $OR^1$, $CO_2R^2$, NO2, or a phenyl, phenoxy, or 2-pyridinyloxy group each optionally containing up to 3 compatible substituents selected from F, Cl, Br, CH3, and CF3;

Y represents H, F, Cl, Br, I, $R^1$, or $CO_2R^2$;

Z represents H, F, Cl, Br, I, or $R^1$;

$R^1$ represents $C_1$-$C_4$ alkyl optionally containing one or more chloro or fluoro substituents; and $R^2$ represents H, $C_1$-$C_4$ alkyl, $C_3$-$C_4$ alkenyl, or $C_3$-$C_4$ alkynyl, each optionally containing up to four compatible substituents selected from chloro, fluoro, $OR^1$, and phenyl which comprises the consecutive steps of a) contacting 5-amino-3-mercapto-1,2,4-triazole with a suitable acylating agent selected from a carboxylic acid chloride, a carboxylic acid anhydride, and a carboxylic acid (RCOCl, (RCO)₂O, or RCO₂H wherein R is as defined hereinabove) in an essentially non-aqueous medium and heating at a temperature of about 50° C. to about 180° C. to obtain the thermodynamically most stable mono-acylated product, a 5-acylamino-3-mercapto-1,2,4-triazole compound of the formula

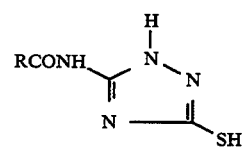

wherein R is as defined hereinbefore;

b) contacting said 5-acylamino-3-mercapto-1,2,4-triazole compound with chlorine in a medium containing an aqueous acid under conditions conducive to the formation of a 5-acylamino-3-chlorosulfonyl-1,2,4-triazole compound of the formula

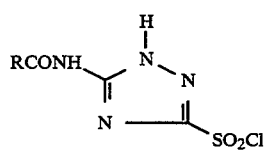

wherein R is as defined hereinabove; and c) contacting said 5-acylamino-3-chlorosulfonyl-1,2,4-triazole compound with a substituted aniline compound of the formula

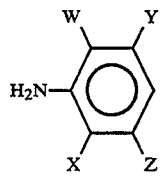

wherein W, X, Y, and Z are as defined hereinabove under conditions conducive to the formation of said 5-acylamino-1,2,4-triazole-3-sulfonamide compound.

2. A process according to claim 1 wherein formic acid or acetic acid containing about 2 to about 10 moles of water per mole of 5-acylamino-3-mercapto-1,2,4-triazole is employed in the medium in step b and steps b and c are carried out without recovery of the 5-acylamino-3-chlorosulfonyl-1,2,4-triazole compound prepared from the mixture obtained in step b.

3. A process according to claim 1 wherein acetic acid containing about 2 to about 10 moles of water per mole of 5-acylamino-3-mercapto-1,2,4-triazole is employed in the medium in step b, and acetic anhydride is employed as the acylating agent in step a and steps a and b are carried out without recovery of the 5-acylamino-3-mercapto-1,2,4-triazole compound prepared from the mixture obtained in step a.

4. A process according to claim 1 wherein acetic acid containing about 2 to about 10 moles of water per mole of 5-acylamino-3-mercapto-1,2,4-triazole is employed in the medium of step b, acetic anhydride is employed as the acylating agent in step a, and steps a, b and c are carried out without recovery of the 5-acylamino-3-chlorosulfonyl-1,2,4-triazole and 5-acylamino-3-mercapto-1,2,4-triazole compounds prepared from the mixtures obtained in steps b and a, respectively.

5. A process according to claim 1 wherein the medium in step b comprises about 1 to about 37 percent aqueous hydrochloric acid.

6. A process according to claim 1 wherein the medium in step b contains aqueous formic acid or acetic acid.

7. A process according to claim 6 wherein the medium contains about 2 to about 10 moles of water per mole of 5-acylamino-3-mercapto-1,2,4-triazole compound.

8. A process according to claim 1 wherein the process step b is conducted at a temperature of about $-15°$ C. to about $30°$ C.

9. A process according to claim 1 wherein the 5-acylamino-3-chlorosulfonyl-1,2,4-triazole compound prepared is employed as an intermediate without recovery from the mixture obtained.

* * * * *